United States Patent
Sampson et al.

(10) Patent No.: US 9,358,543 B2
(45) Date of Patent: Jun. 7, 2016

(54) VESSEL HOLDER AND CAP ASSEMBLY

(71) Applicant: Covaris, Inc., Woburn, MA (US)

(72) Inventors: Jonathan Sampson, Lynn, MA (US); James A. Laugharn, Jr., Winchester, MA (US); Ion A. Tsinteris, Somerville, MA (US)

(73) Assignee: Covaris, Inc., Woburn, MA (US)

(*) Notice: Subject to any disclaimer, the term of this patent is extended or adjusted under 35 U.S.C. 154(b) by 0 days.

(21) Appl. No.: 14/534,665

(22) Filed: Nov. 6, 2014

(65) Prior Publication Data
US 2015/0132841 A1    May 14, 2015

Related U.S. Application Data

(60) Provisional application No. 61/901,760, filed on Nov. 8, 2013.

(51) Int. Cl.
| | | |
|---|---|---|
| *B01L 9/06* | (2006.01) | |
| *B01L 3/00* | (2006.01) | |
| *G01N 1/28* | (2006.01) | |

(52) U.S. Cl.
CPC .............. *B01L 9/06* (2013.01); *B01L 3/50853* (2013.01); *B01L 3/50855* (2013.01); *B01L 3/50825* (2013.01); *B01L 2200/025* (2013.01); *B01L 2200/0689* (2013.01); *B01L 2300/042* (2013.01); *B01L 2300/043* (2013.01); *G01N 2001/2866* (2013.01)

(58) Field of Classification Search
CPC ............ B01L 3/50853; B01L 3/50825; B01L 2200/025; B01L 2300/042
See application file for complete search history.

(56) References Cited

U.S. PATENT DOCUMENTS

| | | | | |
|---|---|---|---|---|
| 4,126,223 A * | 11/1978 | Griffin | ................ | B01L 3/50215 206/445 |
| 4,599,314 A * | 7/1986 | Shami | ................ | B01L 3/50853 206/509 |
| 5,110,556 A * | 5/1992 | Lyman | ................ | B01L 3/50255 356/246 |
| 5,112,574 A * | 5/1992 | Horton | ................ | B01L 3/5085 215/364 |
| 6,436,351 B1 * | 8/2002 | Gubernator | ......... | B01J 19/0046 210/257.2 |
| 6,455,005 B1 * | 9/2002 | Berray | ................ | B01L 3/50853 215/247 |
| 6,890,488 B2 * | 5/2005 | Mathus | ............... | B01L 3/50853 422/550 |
| 2005/0236346 A1 * | 10/2005 | Whitney | ................... | B01L 9/06 211/74 |
| 2007/0297950 A1 * | 12/2007 | Hochstrasser | ...... | B01L 3/50853 422/400 |

\* cited by examiner

*Primary Examiner* — Paul Hyun
(74) *Attorney, Agent, or Firm* — Wolf, Greenfield & Sacks, P.C.

(57) ABSTRACT

A vessel holder assembly is provided. A vessel holder, for receiving one or more vessels, includes a first set of attachment features. A cap assembly, for covering the vessel(s) includes a second set of attachment features. Respective attachment features of the vessel holder and the cap assembly may be complementary, such that engagement between complementary attachment members results in an attachment between the cap assembly and the vessel holder. Such an attachment may be manually removable, or may be locked so as to require a tool, or other suitable method, for detaching the cap assembly from the vessel holder.

31 Claims, 15 Drawing Sheets

VESSEL HOLDER AND CAP ASSEMBLY

RELATED APPLICATION

This application claims the benefit of U.S. Provisional Application No. 61/901,760 filed Nov. 8, 2013, entitled "VESSEL HOLDER AND CAP ASSEMBLY," the entire contents of which is incorporated herein by reference.

BACKGROUND

Biological analysis often requires a number of processing steps which may lead to loss or contamination of sample material. For example, it may desirable for certain cellular components within the blood, such as nucleic acids or proteins, to be analyzed or processed. Accordingly, to carry out such an analysis, a blood sample is collected, blood cells within the sample are lysed, and the sample is sterilized.

Using conventional methods, however, each of the above steps involve transfer of the sample from one container to another. That is, the blood sample is transferred into a container and then lysed, chemically or mechanically. After lysis, the cellular contents are moved to another container for centrifugation, and subsequently transferred to yet another container for sterilization. Once the desired cellular contents are sterilized, then the appropriate analysis is conducted. During the course of transferring sample contents from one location to another, invariably, some sample material will be lost or exposed to a risk of contamination. Thus, it is desirable for such risks to be minimized.

SUMMARY

The inventors have appreciated that it would be advantageous for each of the steps in preparing a sample for analysis to be carried out within a single container. For example, a sample (e.g., tissue, blood, chemical formulation, etc.) may be introduced into a vessel held within a vessel holder assembly, which includes a vessel holder capped and sealed by a cap assembly, so as to prevent sample loss and/or contamination. In some embodiments, while within the vessel, the sample material may be subject to focused acoustic treatment, resulting in cellular lysis, fragmentation and/or sterilization. Accordingly, aspects of the present disclosure may provide desirable conditions through which samples located within the vessels held by the combined vessel holder and cap assembly may be acoustically processed, yielding favorable results.

A vessel holder may have a base for holding a vessel, within which sample material may be introduced. In some embodiments, the base includes one or more receptacles each for receiving the vessel(s); or the vessel(s) may be provided with the base (e.g., formed integrally together with the base, pre-attached to the base). The vessel holder may have a number of attachment members that are located on the base, for forming a suitable attachment with complementary attachment members of a cap assembly.

Any suitable attachment member(s) may be employed, as the scope of the present disclosure should not be limited in this respect. The attachment member(s) may be structured or otherwise shaped in an appropriate manner. In some embodiments, the attachment member(s) may include cantilever-type arms, interlocking members, protrusions, tabs, bayonet features, inserts, fasteners, snap-fit flanges, openings/slots having a shape through which any of the above may enter, etc. For example, the attachment member(s) may include a protrusion or tab that extends inwardly from an outer surface of the base, for engaging with a complementary surface of a cap, or associated cap assembly. In various embodiments, the attachment member(s) may be positioned upright relative to the base, may extend alongside the base, or alternatively, the attachment member(s) may include a recess that accommodates entry of a complementary attachment member from a corresponding cap assembly.

One or more caps may be provided in a cap assembly for covering the opening of each vessel held by the vessel holder. In some embodiments, multiple caps are attached to one another. Each cap of a cap assembly may include an upper surface and a wall extending downwardly from the upper surface, so as to provide an enclosure for the entrance of each respective vessel. Each cap may include an attachment member that is complementary to a corresponding attachment member of the vessel holder.

The complementary first and second attachment members of a respective vessel holder and cap assembly may be arranged to engage with one another so as to form an attached arrangement between the cap assembly and the vessel holder, creating resistance to relative movement between the cap assembly and the vessel holder away from one another, while the cap(s) cover the respective opening(s) of the respective vessel(s).

Similar to that with respect to the vessel holder, the cap assembly may employ any suitable attachment member(s). In some embodiments, the cap assembly may include a protrusion that extends outwardly from the sidewall of a cap, for fitting over a complementary surface of, or otherwise engaging with, an attachment member of the vessel holder. In some embodiments, the attachment member(s) of the cap assembly may include one or more arms that extend downwardly toward and for engaging with the complementary attachment member(s) of the vessel holder. In some embodiments, attachment members of either, or both, the cap assembly and the vessel holder include arms that extend mutually toward one another, for forming a suitable attachment between the cap assembly and vessel holder.

In some embodiments, attaching the cap assembly and the vessel holder together may involve appropriately orienting the cap assembly and vessel holder relative to one another and pressing them together so that the cap assembly forms a snap fit with the vessel holder. In some embodiments, when the cap assembly and the vessel holder are brought together, the sidewall of the cap(s) and/or upright attachment arms of the vessel holder may flex appropriately away from one another so that respective surfaces (e.g., protrusions, tabs, recessed regions) of the cap assembly and vessel holder are able to slide over and past one another. Once protruding surfaces are cleared, one or more attachment members (e.g., upright arms) may return back to a position that results in a suitable attachment between the cap assembly and vessel holder.

A sealing material (e.g., rubber/teflon/polymer septum) may be located within the enclosure provided by each cap. As a result, when a vessel is held within a receptacle of the vessel holder, installation of the cap and the vessel holder together results in the formation of a seal at the vessel entrance so that loss and/or contamination of sample material within the vessel is substantially prevented.

In some embodiments, engagement between the complementary first and second attachment members forms a locked arrangement between the cap assembly and the vessel holder. That is, once the cap assembly is snapped on to the vessel holder so as to cover and seal the vessel(s), the cap(s) and the vessel holder are locked in place, unable to be pulled apart without a supplemental method of detachment. For example, a switch or tool may be used to disengage the otherwise locked cap assembly and vessel holder from one another.

Aspects of the present disclosure may include a tool used for detaching the cap assembly from the vessel holder. In some embodiments, an upright portion of the tool may be pushed into an opening of the vessel holder so that an upper surface of the tool slides along a portion of the cap assembly (e.g., slanted lower surface of a cap that complements the tool). Such sliding may cause respective attachment surfaces of the cap and the vessel holder to move apart from one another and, thus, disengage.

In some embodiments, the tool includes a base having a plurality of openings aligned with the receptacles, or vessels, of the vessel holder and through which respective vessels may enter. Such openings allow for the cap assembly to be disengaged from the vessel holder while the vessel holder is holding one or more vessels. The tool may also include a number of detachment members, each positioned upright relative to the base. For some embodiments, such detachment members may be positioned similarly to upright attachment members of the vessel holder. Though, the upright detachment members of the tool may be appropriately positioned on the base of the tool so as to allow for alignment with corresponding openings of the vessel holder, through which the upright detachment members may access the attached cap assembly. In some embodiments, the protrusion(s) of the cap includes a lower surface that is slanted or otherwise shaped to receive a complementary upper surface of the detachment member(s) of the tool. Accordingly, the cap assembly and the vessel holder may be detached when a detachment member of the tool is pushed up against a corresponding surface of the cap assembly and/or vessel holder.

In an illustrative embodiment, a vessel holder assembly is provided. The vessel holder assembly includes a vessel holder including a base for holding a plurality of vessels, the vessel holder including at least one first attachment member located on the base; and a cap assembly including a plurality of caps attached together, each cap arranged to cover an opening of a respective vessel held by the base, the cap assembly including at least one second attachment member complementary to a corresponding first attachment member such that engagement between the complementary first and second attachment members forms an attachment that resists relative movement between the cap assembly and the vessel holder away from one another.

In another illustrative embodiment, a vessel holder is provided. The vessel holder includes a base having a region for holding a plurality of vessels; and a plurality of attachment members surrounding the region for holding the plurality of vessels, each attachment member complementary to a corresponding attachment member of a cap assembly, for forming an attachment that resists relative movement between the cap assembly and the vessel holder away from one another.

In a further illustrative embodiment, a cap assembly is provided. The cap assembly includes a plurality of caps attached together, each cap arranged to cover an opening of a respective vessel; and a plurality of attachment members, each attachment member complementary to a corresponding attachment member of a vessel holder, for forming an attachment that resists relative movement between the cap assembly and the vessel holder away from one another.

In yet another illustrative embodiment, a tool for detaching a cap assembly from a vessel holder is provided. The tool includes a base having a plurality of openings; and a plurality of detachment members, each detachment member extending upright relative to the base and having an upper surface adapted to slide along a surface of the cap assembly, to disengage respective attachment members of the cap assembly and the vessel holder.

In another illustrative embodiment, a method of detaching a cap assembly from a vessel holder is provided. The method includes pushing an upright detachment member through an opening of a vessel holder such that an upper surface of the upright detachment member slides along a surface of the cap assembly, causing disengagement of respective attachment members of the cap assembly and the vessel holder.

In a further illustrative embodiment, a vessel holder assembly is provided. The vessel holder assembly includes a vessel holder including a base for holding a vessel, and at least one first attachment member located on the base; a cap arranged to cover an opening of the vessel held by the base; and at least one second attachment member adjacent the cap, complementary to a corresponding first attachment member such that engagement between the complementary first and second attachment members forms an attachment that resists relative movement between the cap and the vessel holder away from one another.

In some embodiments, an acoustic energy source is spaced from and exterior to the vessel, and the acoustic energy comprises a frequency of between about 100 kilohertz and about 100 megahertz and a focal zone having a width of less than about 2 centimeters, and wherein at least a portion of the acoustic energy is adapted to propagate exterior to the vessel.

Other advantages and novel features of the invention will become apparent from the following detailed description of various non-limiting embodiments when considered in conjunction with the accompanying figures and claims.

BRIEF DESCRIPTION OF DRAWINGS

Aspects of the invention are described with reference to illustrative embodiments shown in the drawings, in which like numbers reference like elements, and wherein.

DETAILED DESCRIPTION

Figure 1:
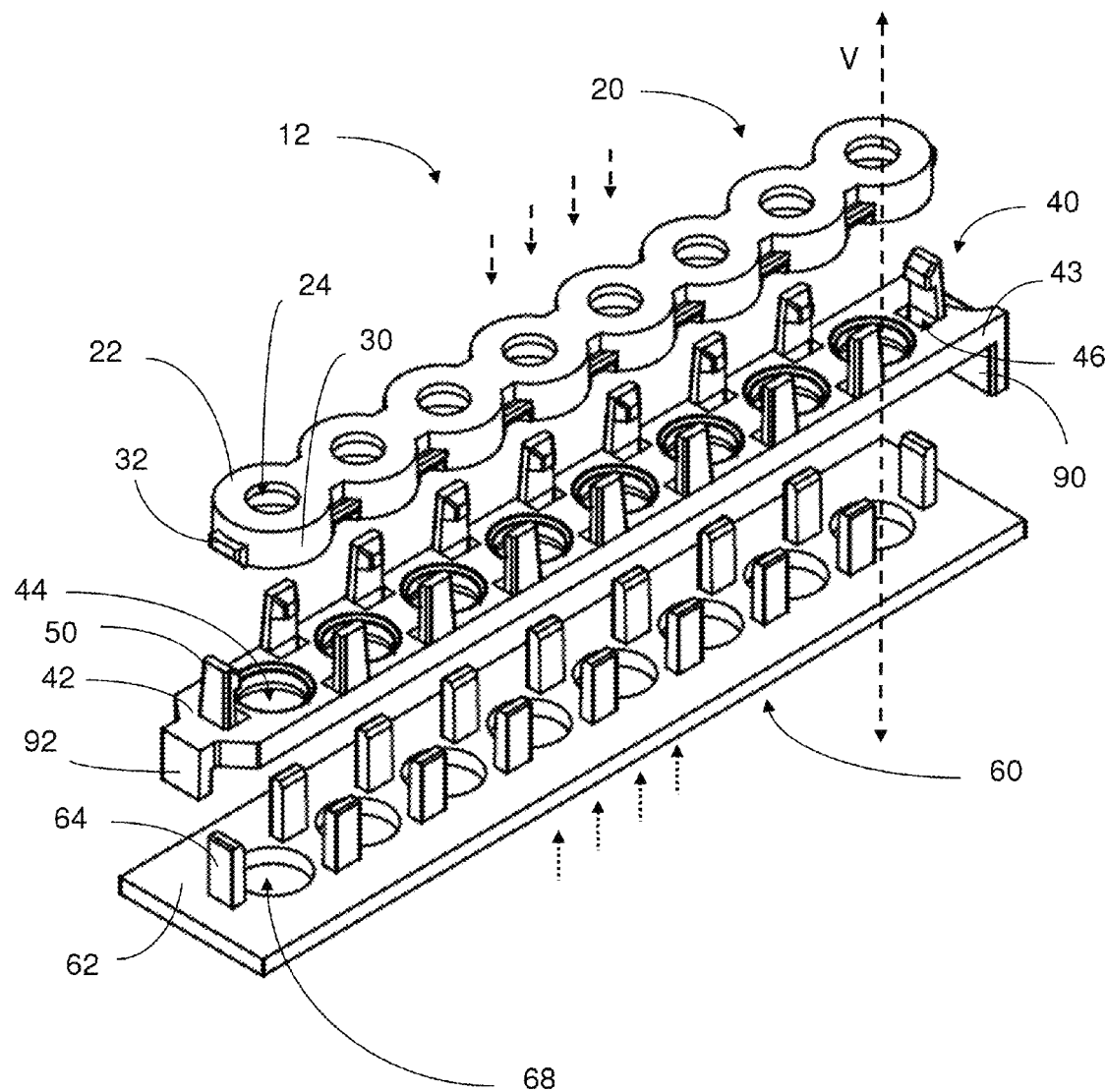
FIG. 1 shows an exploded perspective view of a vessel holder assembly in accordance with some embodiments.

It should be understood that illustrative embodiments are described in accordance with aspects of the invention. However, the embodiments described are not necessarily intended to show or incorporate all aspects of the invention, but rather are used to describe a few illustrative embodiments. Thus, aspects discussed herein are not intended to be construed narrowly in view of the illustrative embodiments. In addition, it should be understood that aspects of the invention described may be used alone or in any suitable combination with other aspects also described.

The present disclosure relates to a vessel holder assembly that may be used for processing, treating and/or analyzing sample materials contained within vessels held by the assembly. For example, the vessel holder assembly may provide suitable conditions under which sample material may be subject to focused acoustic treatment.

The vessel holder assembly may include a vessel holder and a cap assembly, each having complementary features that provide for attachment between the vessel holder and cap assembly. In some cases, the location of engagement between attachment features of the vessel holder and cap assembly may occur apart from the vessel itself. That is, for some embodiments, when installed, the cap assembly may be appropriately positioned so as to cover and seal respective vessel entrances, however, the features that serve to resist separation of the caps from the vessels, and thus exposure of the sample contents therein, may be located on the cap assembly and the vessel holder, rather than on the vessel, or solely on the vessel, itself.

The base of the vessel holder may include receptacles within which vessels may be placed. Or, the vessels may be pre-attached to the base, or formed integrally with the base. The vessel holder may also include a first set of attachment members (e.g., arms, protrusions, tabbed features, sockets, recesses, flanges, etc.), for engaging with complementary attachment members of a cap assembly.

The cap assembly includes caps that are arranged to cover vessels held by the vessel holder. As noted above, the cap assembly may include a second set of attachment members that are complementary to the first set of attachment members. Engagement between the two sets of attachment members results in an attachment that resists separation of the cap assembly from the vessel holder. In some embodiments, engagement between the two sets of attachment members results in a locked attachment between the cap assembly and the vessel holder, requiring a tool or other detachment method for disengaging the cap assembly and the vessel holder from one another.

FIGS. 1-5 depict an illustrative embodiment of a vessel holder assembly 12 that incorporates one or more aspects of the present disclosure. The vessel holder assembly 12 includes a cap assembly 20 and a vessel holder 40. The vessel holder assembly 12 may optionally include a tool 60 used to detach the cap assembly from the vessel holder 40.

In the embodiment depicted, the vessel holder assembly is arranged as a strip that allows for 8 different vessels to be held within its receptacles. Though, it can be appreciated that the vessel holder assembly may be constructed to accommodate any suitable number of vessels, in any appropriate configuration. For example, the vessel holder assembly may be arranged as a plate for holding vessels in rows and columns, or in any other configuration. Alternatively, the vessel holder assembly may be arranged to hold a single vessel.

Figure 2:
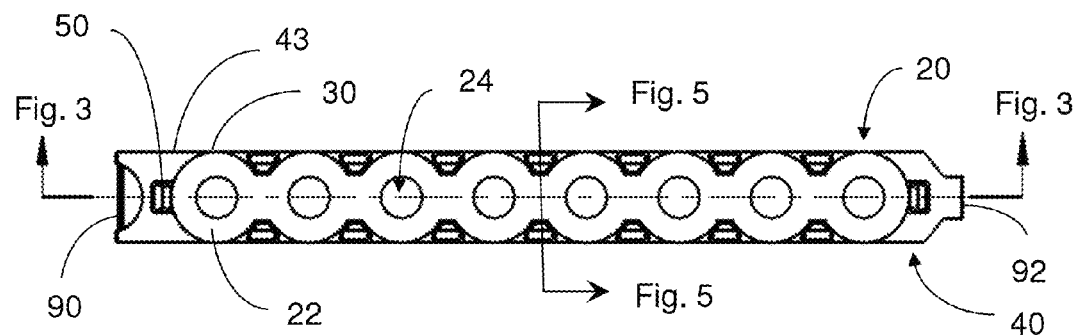
FIG. 2 depicts a top view of a vessel holder assembly in accordance with some embodiments.
Figure 3:
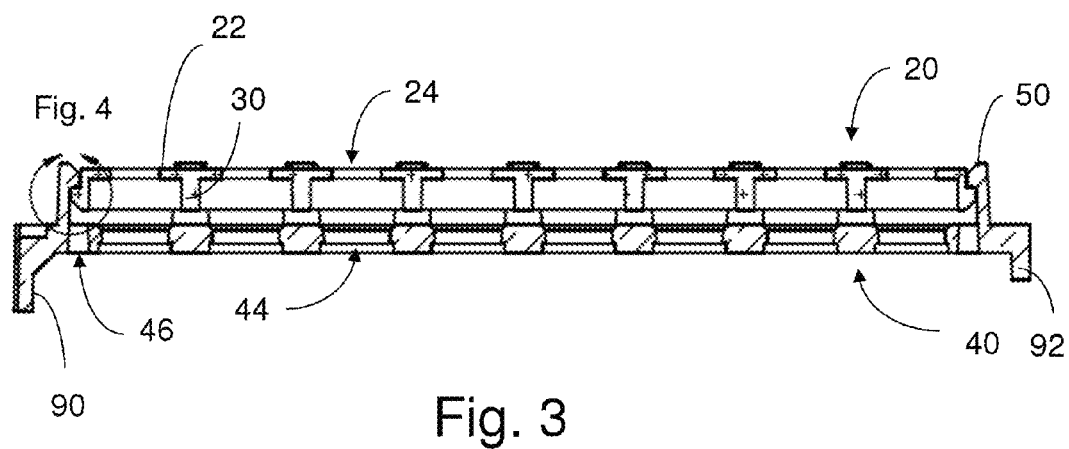
FIG. 3 illustrates a cross-sectional view of the vessel holder assembly of FIG. 2.

While other cap arrangements may be employed, the cap assembly 20 of the illustrated embodiment includes a row of interconnected caps. As shown, each cap has an upper surface 22 and a curved sidewall 30 that extends downwardly from the upper surface, defining a partial enclosure for covering a vessel entrance. In some embodiments, as shown in FIGS. 1-2, the sidewall 30 of each cap may be substantially cylindrical, though, it can be appreciated that the sidewalls may be shaped appropriately based on the entrance of the vessel to be covered and sealed, which may have a circular or non-circular shape.

Each cap may also include an opening 24 that provides access to the vessel, for example, for introducing sample material into the vessel or removing material therefrom (e.g., via a rubber septum). The cap assembly includes a number of attachment members 32, illustrated in this embodiment to be protrusions that extend from the sidewall 30 of the caps. The attachment members 32 have a structure that is suitable to engage with corresponding attachment members 50 of the vessel holder 50, each having a complementary surface to form an attachment between the cap assembly and the vessel holder.

While several attachment members 32 of the cap assembly are shown to be located between adjacent caps, notwithstanding attachment members located at opposing ends of the strip, it can be appreciated that attachment members of the cap assembly may be positioned and oriented in any suitable manner. For instance, attachment members 32 of the cap assembly may be located on the curved sidewalls 30 of the caps in addition to, or rather than, being located in between the curved sidewalls.

As shown, the cap assembly may be press fit toward the vessel holder, along the downward direction illustrated by the dashed arrows. A suitable attachment between the cap assembly and the vessel holder may be made when one or more vessels are suitably situated within receptacles of the vessel holder. The cap assembly may be press fit using any suitable method, for example, by manual compression, clamping tools, compression roller, etc.

The vessel holder 40 includes a base 42 that includes a number of receptacles 44 disposed along a strip defined by the base, each receptacle suited to receive a respective vessel therein. The embodiment illustrates attachment members 50 surrounding the row of receptacles 44. The attachment members 50 are positioned so as to be aligned with complementary attachment members 32 of the cap assembly 20. As discussed above, in some embodiments, the vessel holder may include vessels integrally formed with the base.

In this embodiment, the attachment members 50 of the vessel holder are positioned upright relative to the base 42 such that when complementary attachment members of the cap assembly and the vessel holder engage, and a suitable seal is formed over the opening of the vessel held within the vessel holder, the cap assembly remains a distance D above the base 42 of the vessel holder 30. In some embodiments, the distance D is equivalent to the height of an upper flange of a vessel that rests on the surface of the base. To provide more active control of the temperature of the sample, during focused acoustic processing, this distance D may allow for the vessel to be exposed to a greater amount of coupling medium (i.e., cooling fluid) surrounding the vessel than would otherwise be the case without such separation. That is, for some embodiments, the position of the lower side of the cap, offset from the base 42, may accommodate fluid flow around the vessel, for cooling thereof and, thus, the contents within the vessel.

As further shown in this embodiment, each of the attachment members 50 of the vessel have a protrusion 52 that extends inward from an outer surface 43 of the base 42. Accordingly, referring to FIGS. 4 and 5, the attachment members 50 have inwardly extending protrusions 52 with surfaces that are suitable to engage with complementary protruding surfaces of attachment members 32 of the cap assembly. As depicted, the protrusion 52 of the attachment member 50 has a slanted lower surface 54, a slanted upper surface 56 and a vertically-oriented surface 58; and the protrusion 32 has a substantially level upper surface 34, a slanted lower surface 36 and a vertically-oriented surface 38. As discussed below, each of the above surfaces of the respective attachment members may accommodate engagement of the cap assembly and the vessel holder. It can be appreciated that other surface configurations may be possible, as the present disclosure is not limited in this regard.

Accordingly, respective attachment members of the cap assembly and vessel holder may be placed into engagement by appropriately aligning and then pressing the cap assembly and vessel holder toward one another. The upright portion of the attachment members 50 of the vessel holder 40 and/or the sidewall 30, or other portion, of the cap assembly may be exhibit a suitable degree of flexibility so as to accommodate sliding of complementary protrusions past one another during engagement.

The shape of the respective attachment members may also help to allow for mutual engagement between the cap assembly and vessel holder. That is, when the cap assembly and vessel holder are pressed toward one another, respective slanted surfaces 36, 56 of the cap assembly and vessel holder come into contact and are shaped so that the respective protrusions 32, 52 are able to slide past one another without substantial compressive force. During such sliding, attachment member 50 flexes back outwardly to allow for the cap assembly 20 to move further downward toward the base 42. As the cap assembly moves further into engagement with the vessel holder, respective vertically-oriented surfaces 38, 58 may then come into contact and slide past one another. Upon clearance of the surfaces 38, 58, the upright attachment members 50 and/or cap sidewalls 30 are able to fall back into their equilibrium position as corresponding protrusions 32, 52 are suitably engaged along surfaces 34, 54.

Attachment between the cap assembly and vessel holder, in accordance with the present disclosure, may be suitable to resist relative movement between the cap assembly and the vessel holder away from one another, for example, along the vertical axis V.

As shown in this embodiment, the attachment members 50 are oriented so as to exhibit a resting position that forms a slight angle, offset from the vertical axis V. That is, the attachment members 50 are tilted slightly inward away from the outer surface 43 of the base 42, allowing for a relatively secure attachment to be established between the cap assembly and the vessel holder.

In some embodiments, upon suitable engagement, the cap assembly and the vessel holder are attached together, but may be pulled apart with a relatively small amount of force. For example, the slanted surface 54 of the upright attachment member 50 serves to guide the attachment member in being flexed outwardly relative to the sidewall 30 when the cap assembly and the vessel holder are pulled apart. Accordingly, when the degree of slant of the surface 54 is greater, the force required to disengage the cap assembly and the vessel holder is less. Conversely, the force required to disengage the cap assembly and the vessel holder is greater when the surface 54 exhibits a smaller degree of slant, i.e., closer to a substantially level surface. In some embodiments, attachment members may be structured such that upon suitable engagement, the cap assembly and vessel holder are locked together, as described further below.

It can be appreciated that other arrangements of the vessel holder assembly are possible and within the scope of the present disclosure. For example, in some embodiments, attachment members 50 of the vessel holder do not extend upright relative to the base. Rather, in a reverse configuration (not shown in the figures), the sidewalls 30 of the cap assembly, or other attachment arm-like features, may extend down from the upper surface 22 so as to engage with complementary attachment member(s) on the base of the vessel holder. For example, the base may have a recess with a corresponding snap fit feature for receiving/attaching with a downwardly extending sidewall and/or attachment arm. In some embodiments, the sidewall, or other arm-like feature, may extend from the upper surface of the cap assembly to engage the vessel holder in a bayonet-type attachment.

As discussed above, the attachment members 50 of the vessel holder may have upright arms that extend upward toward the cap assembly so as to allow the vessel to be surrounded by cooling fluid. Alternatively, in some embodiments, arms may extend downwardly from the cap assembly while also permitting cooling fluid to surround the vessel. For example, the arms may extend downwardly from the outer periphery of the cap assembly so as to engage with the outer surface 43 of the base 42.

Vessel holder assemblies in accordance with the present disclosure may have other features, for example, for assisting with alignment and/or identification of the assembly. For instance, the vessel holder to optionally include tabs 90, 92 that extend from respective ends of the base 42. These tabs may be used for various purposes, such as for identifying the vessel holder assembly and/or to assist in alignment of various components of the vessel holder assembly (e.g., aligning the vessel holder 40 with a tool 60 for detaching the vessel holder from the cap assembly 20). For example, a barcode may be placed on tab 90, which may be used for identification purposes. Or, tab 92 may be shaped so that a detachment tool 60 may be appropriately aligned with respect to the vessel holder 40 such that upright detachment members 64 are able to easily enter into respective openings 46 of the vessel holder 40.

FIGS. 6-10 illustrate an embodiment of a vessel holder assembly 12 including the vessels 80.

Figure 6:
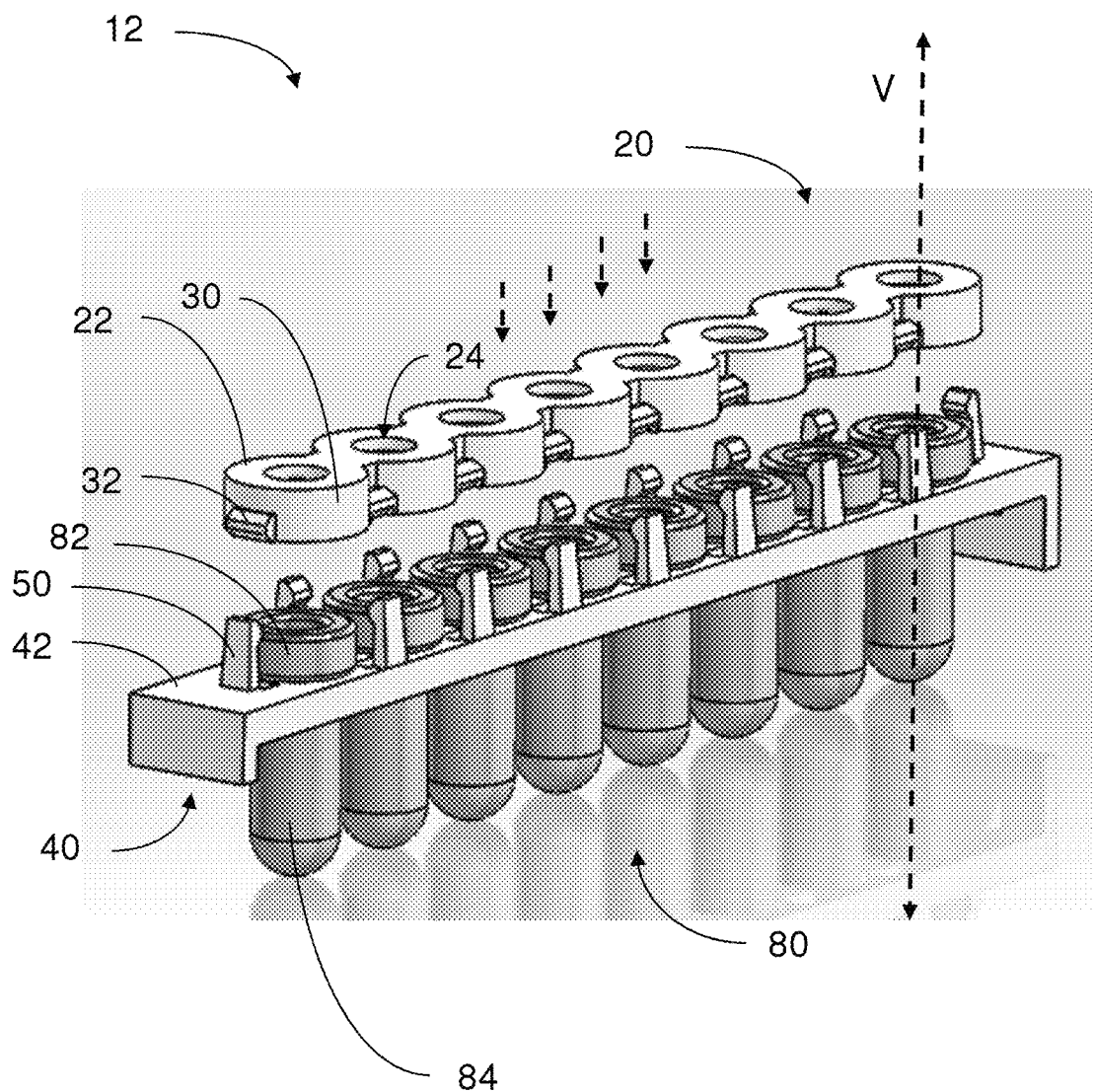
FIG. 6 illustrates a perspective view of a vessel holder assembly in accordance with some embodiments.
Figure 7:
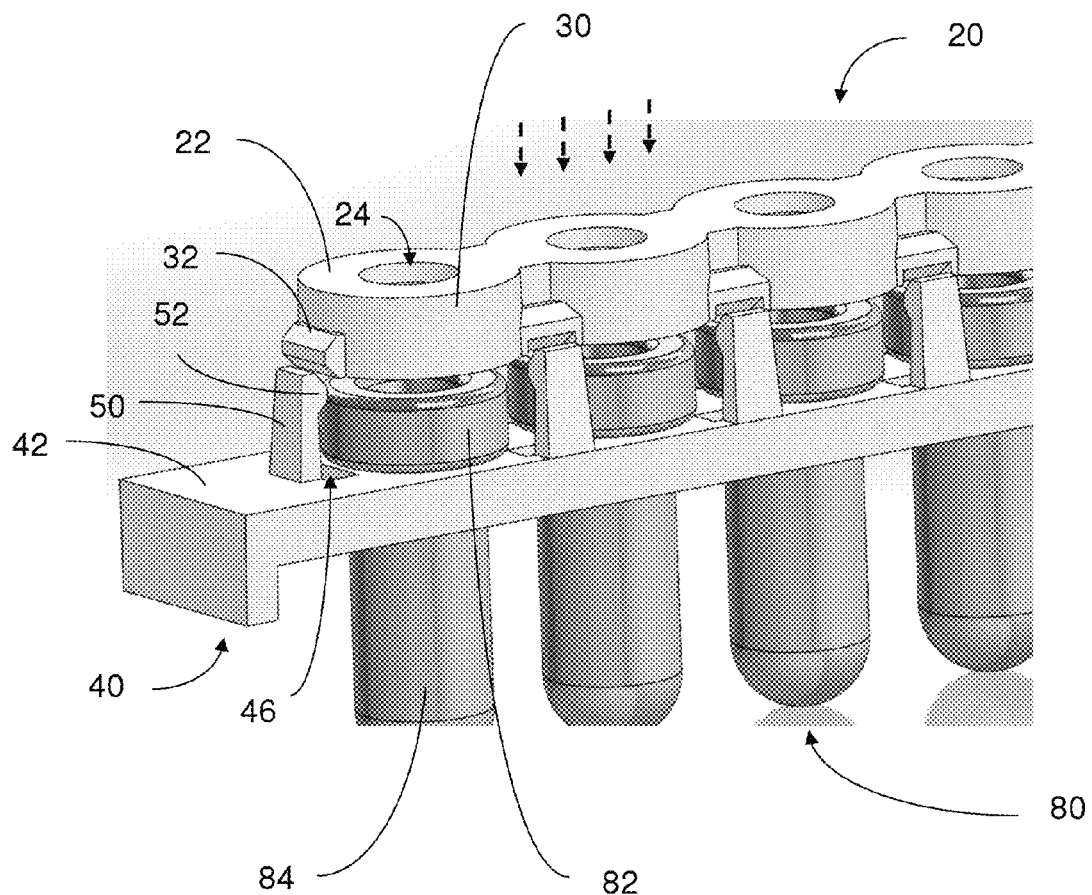
FIG. 7 illustrates a close-up perspective view of the vessel holder assembly of FIG. 6.

As shown in FIGS. 6-7, each of the vessels 80 are located within respective receptacles of the vessel holder 40 prior to attachment with respective caps. Each vessel includes an upper flange 82, upon which the vessel may rest while disposed within the receptacle, and a body 84 within which sample material to be processed may be contained. In some embodiments, the upper flange 82 is appropriately shaped so as to form a press fit attachment with the vessel holder. Or, the upper flange 82 of the vessel may be structured as an overhang having an outer diameter greater than the diameter of the opening of the corresponding receptacle, thus, not permitting the vessel to fall through the respective opening of the vessel holder.

When attaching the cap assembly to the vessel holder, the vessels are first suitably situated within the vessel holder. The cap assembly is then aligned with the vessels and vessel holder, as shown in FIG. 7, and then press fitted with the vessel holder according to the dashed arrows.

Though, it should be appreciated that the present disclosure is not limited to vessel holders having a base with openings, or other receptacles, for receiving separate vessel components. In some embodiments, vessels are formed integral with the base. That is, the vessel holder may include the vessels themselves, in addition to a base having associated attachment members. For example, FIGS. 6-7 show the vessels 80 being held by the vessel holder 40. Such vessels may be "held" by the vessel holder as components that are integral parts of the vessel holder. In some embodiments, the vessel holder and vessels are formed together as a single molded part.

Or, in some cases, the vessels may be separate components that are pre-adhered, or otherwise attached, to the vessel holder. For instance, an adhesive or fasteners may be applied between separate vessels and the base so that the vessels are firmly situated within receptacles of the vessel holder prior to attachment of the cap assembly to the vessel holder.

Figure 8:
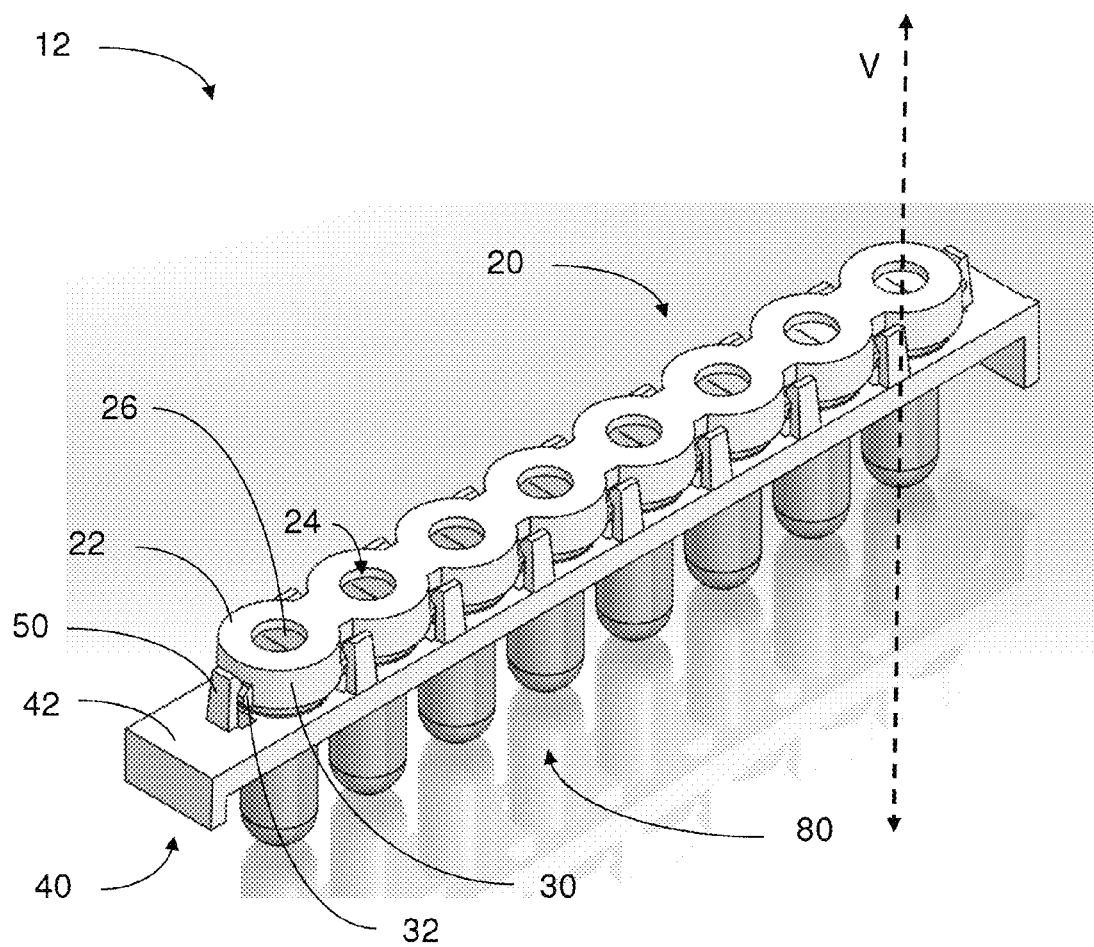
FIG. 8 shows another perspective view of the vessel holder assembly of FIG. 6.
Figure 9:
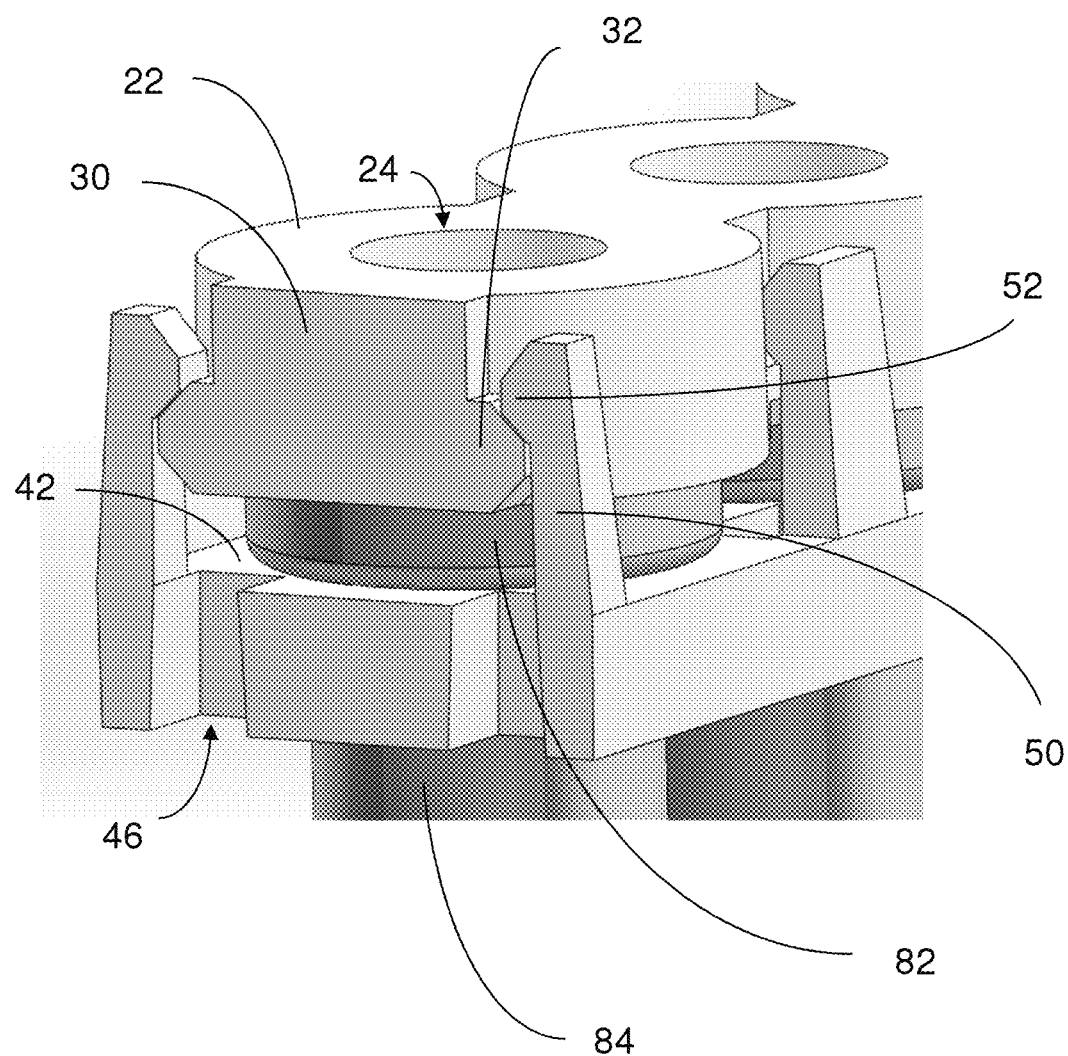
FIG. 9 depicts a cross-sectional perspective view of the vessel holder assembly of FIG. 6.
Figure 10:
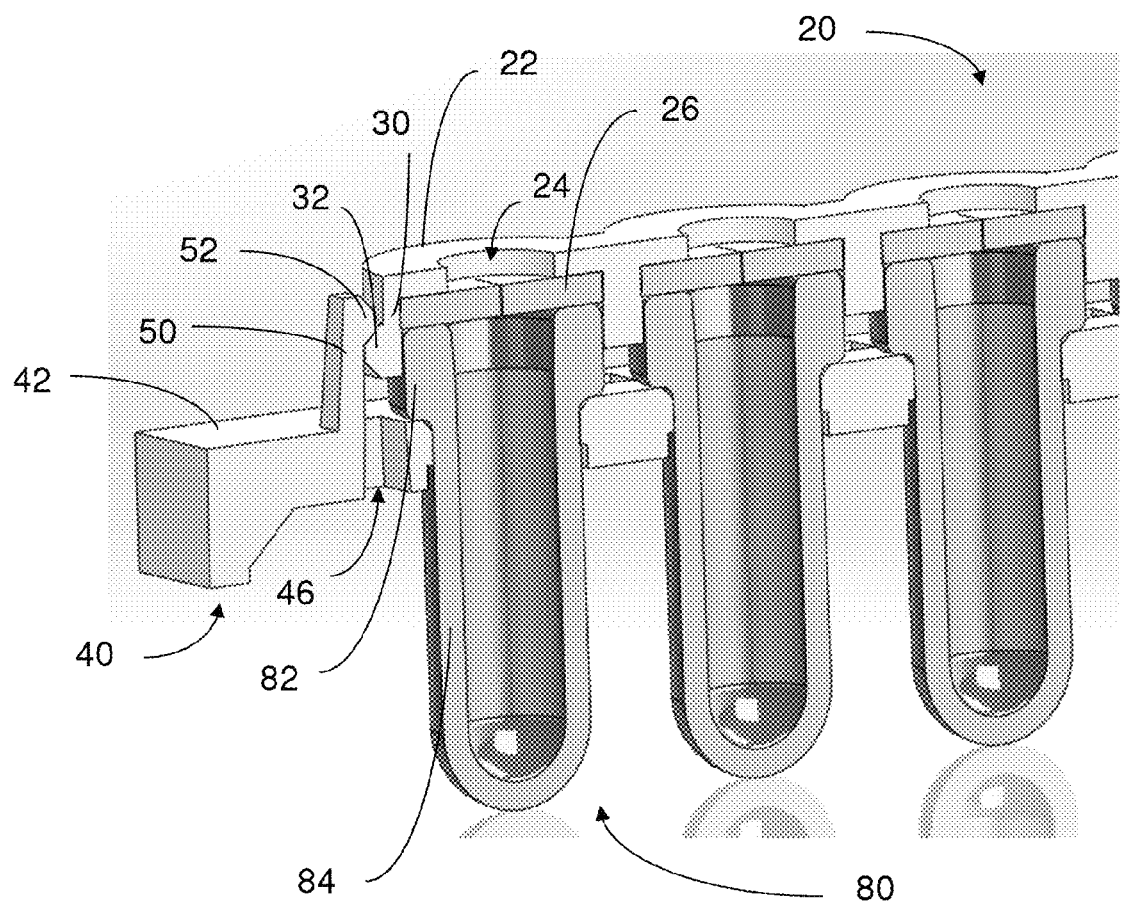
FIG. 10 shows another cross-sectional perspective view of the vessel holder assembly of FIG. 6.

FIGS. 8-10 depict the cap assembly 20 attached to the vessel holder 40, with each cap covering a respective vessel held within receptacles of the vessel holder. A rubber septum 26 is provided within the enclosure of each cap, underneath the upper surface 22 and between sidewalls 30 of the cap. Upon suitable attachment of the cap assembly and vessel holder, a respective septum is pressed up against the top surface of each vessel, creating a seal with the vessel. Though, the septum may allow for sample material to be transferred in and out of the vessel, for example, via a syringe piercing through the septum. Accordingly, when the septum is not pierced, the contents of the vessel are sealed off from the surrounding environment, resulting in a substantial reduction in sample loss and contamination during processing of the sample.

It can be appreciated that other sealing materials may be used, in any appropriate configuration. For instance, caps may be lined with a different type of material, such as silicone or Teflon, which are suitable to form a sufficient seal with the vessel.

FIGS. 9-10 illustrate cross-sectional views of corresponding attachment members of the cap assembly and the vessel holder, appropriately engaged. In this embodiment, the upper surface of the protruding attachment member 32 is slanted, allowing the cap assembly and vessel holder to be more easily disengaged as compared to the embodiments described above in FIGS. 4-5 where the upper surface of the protruding attachment member 32 is substantially level.

FIG. 10 clearly shows the position of a septum 26 between the upper surface 22 of a cap and a vessel 80. As discussed, when corresponding attachment members are suitably engaged, the cap presses against the septum 26, which is in contact with the top surface of the upper flange 82, so as to seal off the internal volume of the vessel 80 from the outside environment. Though, the internal volume of the vessel is accessible through the septum at the opening 24 of the cap, for example, via a syringe (employing a needle) or pipet. Once sample material is introduced or removed from the vessel and the syringe or pipet is removed, a seal is once again formed.

It can be appreciated that any suitable vessel may be held, capped and sealed by the vessel holder assembly. For instance, test tubes, PCR tubes, centrifuge tubes, or any other appropriate vessel may be used in cooperation with vessel holder assemblies described herein. The vessel may be composed of an appropriate material, such as glass (e.g., borosilicate, quartz), plastic, etc.

In some embodiments, the Covaris microTUBE and miniTUBE, which are particularly compatible with systems that employ focused acoustic treatment, may be suitably placed within receptacles of vessel holder assemblies. The microTUBE may be used to treat samples with focused acoustic energy, for example, for shearing nucleic acids and yielding a tight fragment size distribution, disrupting and homogenizing tissues, etc. The microTUBE is made up of a borosilicate glass that provides for low acoustic impedance and high quality acoustic energy transmission. It can be appreciated that any suitable vessel may be used with vessel holders in accordance with the present disclosure.

As discussed above, attachment members of the cap assembly and vessel holder may engage so as to form a locked arrangement. That is, using reasonable force, the cap assembly and vessel holder are unable to be separated without otherwise being unlocked from one another.

Figure 4:
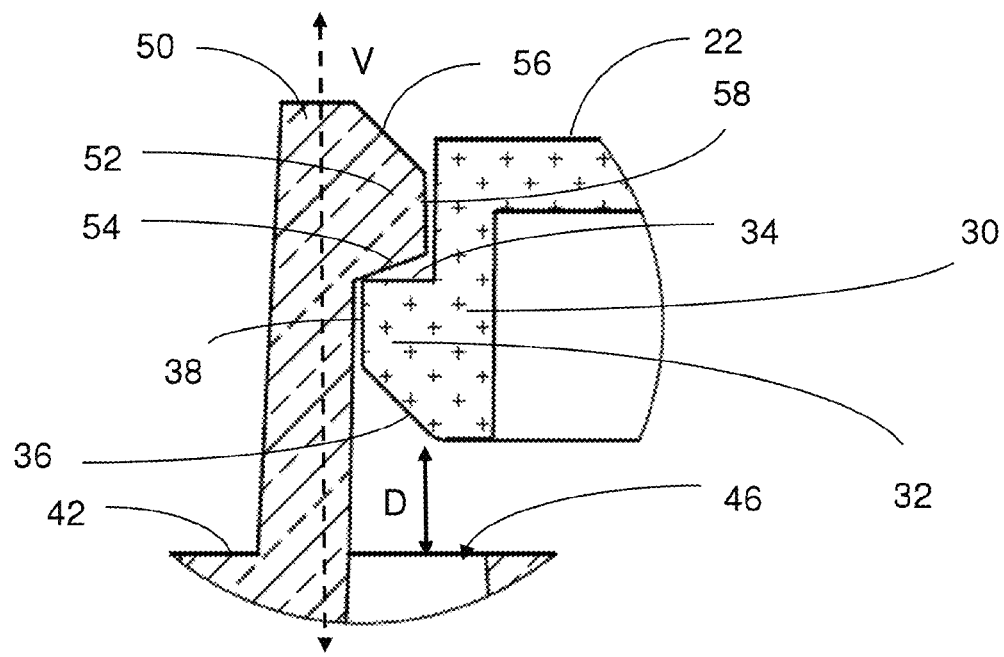
FIG. 4 depicts a close-up view of the cross-section of the vessel holder assembly of FIG. 3.
Figure 5:
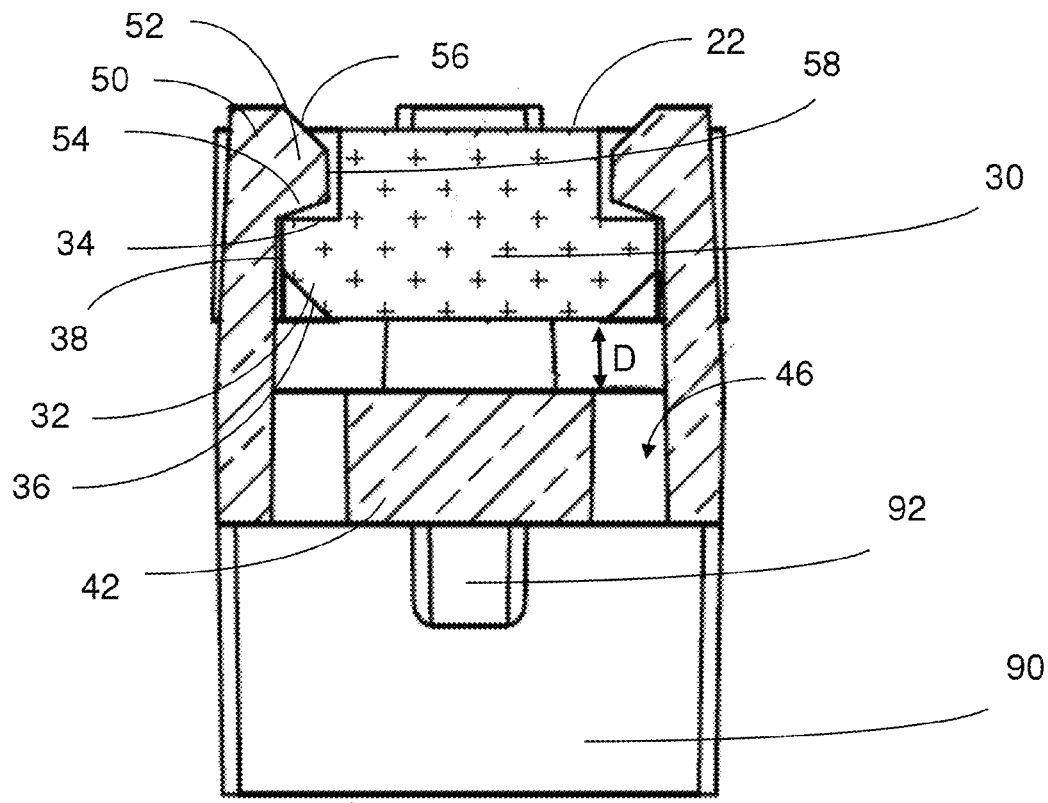
FIG. 5 shows another cross-sectional view of the vessel holder assembly of FIG. 2.
Figure 11:
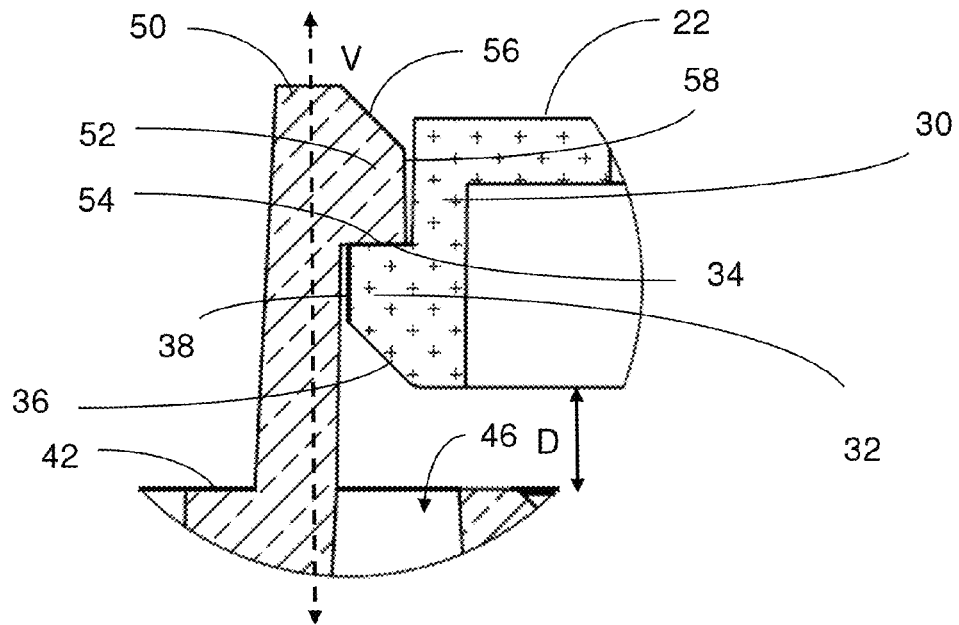
FIG. 11 depicts a close-up view of a cross-section of a vessel holder assembly in accordance with some embodiments.
Figure 12:
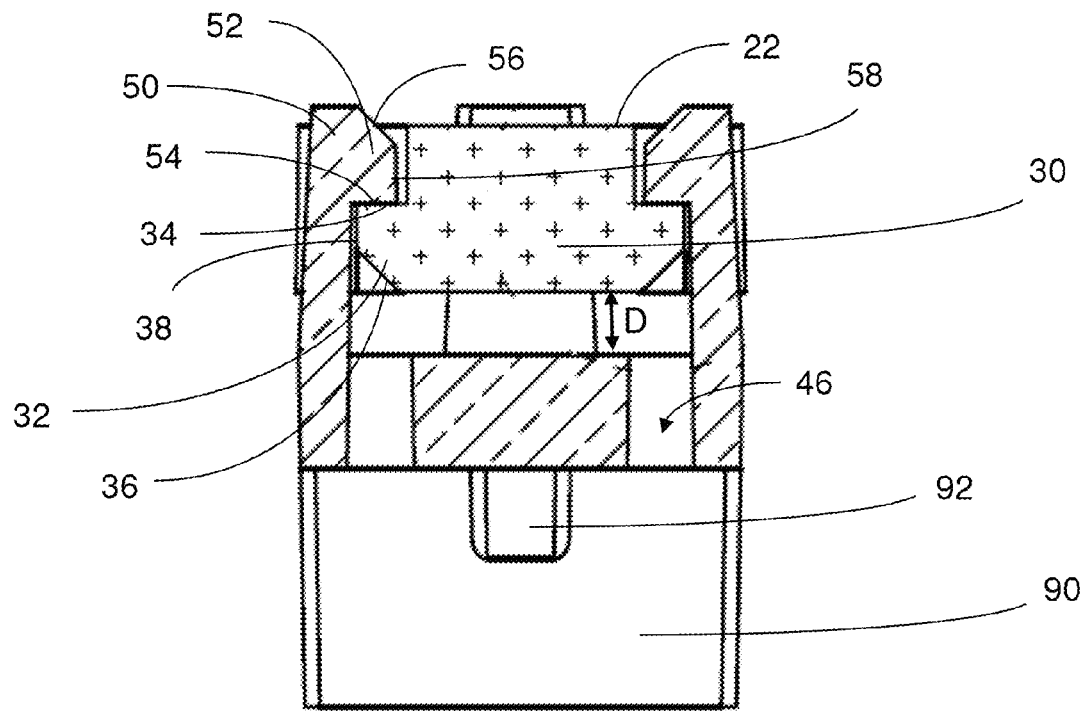
FIG. 12 shows another cross-sectional view of a vessel holder assembly in accordance with some embodiments.
Figure 13:
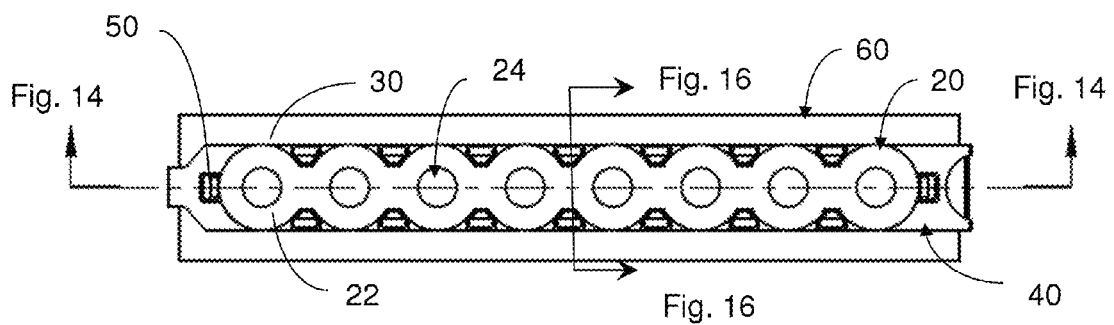
FIG. 13 depicts a top view of a vessel holder assembly in accordance with some embodiments.
Figure 14:
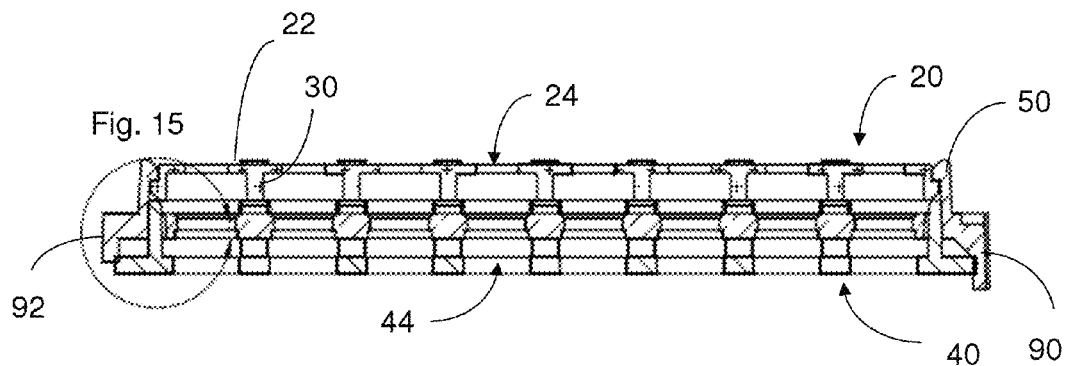
FIG. 14 illustrates a cross-sectional view of the vessel holder assembly of FIG. 13.

An example illustrating how the cap assembly and vessel holder may be locked together is provided below in FIGS. 11-12. The embodiment shown in FIGS. 11-12 differs from the embodiment of FIGS. 4-5 in the degree to which the lower surface 54 of the protrusion 52 is slanted. As described above, the lower surface 54 of the protrusion 52 of the embodiment of FIGS. 4-5 is slightly slanted so as to accommodate removal of the cap assembly from the vessel holder. However, the lower surface 54 of the protrusion 52 of the embodiment of FIGS. 11-12 is substantially level, matching the substantially level surface 34 of protrusion 32. Thus, in this embodiment, when corresponding attachment members 50, 32 are engaged, the cap assembly and the vessel holder are effectively locked in place, unable to be pulled apart using reasonable force. Accordingly, a detachment tool, or other suitable method in which the cap assembly and vessel holder may be unlocked, may be provided.

In some embodiments (now shown in the figures), the lower surface 54 of the protrusion 52 is slanted in a similar direction as that of the upper surface 56, forming a recess underneath the protrusion 52. The upper surface 34 of the protrusion 32 may also be slanted so as to complement the lower surface 54. In this embodiment, the cap assembly and vessel holder are also locked upon mutual engagement of the attachment members.

FIGS. 13-16 show the embodiment of FIG. 1, where the cap assembly and vessel holder are attached to one another, and the detachment tool 60 is also positioned so as to readily detach the cap assembly from the vessel holder. As depicted in FIG. 1, the vessel holder 40 includes a number of openings 46 disposed immediately adjacent to each attachment member 50. The detachment tool 60 includes a base 62 and a number of detachment members 64 oriented upright relative to the base 62. The base also includes openings 68 for vessels 80 to enter therein, permitting the tool to be used whether or not vessels are present within the vessel holder 40.

The tool 60 may be oriented such that each of the detachment members 64 is aligned with and may be inserted into a corresponding opening 46 of the vessel holder 40. Upon insertion of the detachment members 64 into respective openings 46, the tool may be pushed further into engagement with the vessel holder 40, in the direction depicted by the dotted arrows, so as to dislodge the cap assembly 20 from the vessel holder 40. The tool may be pushed into the vessel holder using any suitable method, for example, by manual compression, a clamping tool, etc.

Figure 15:
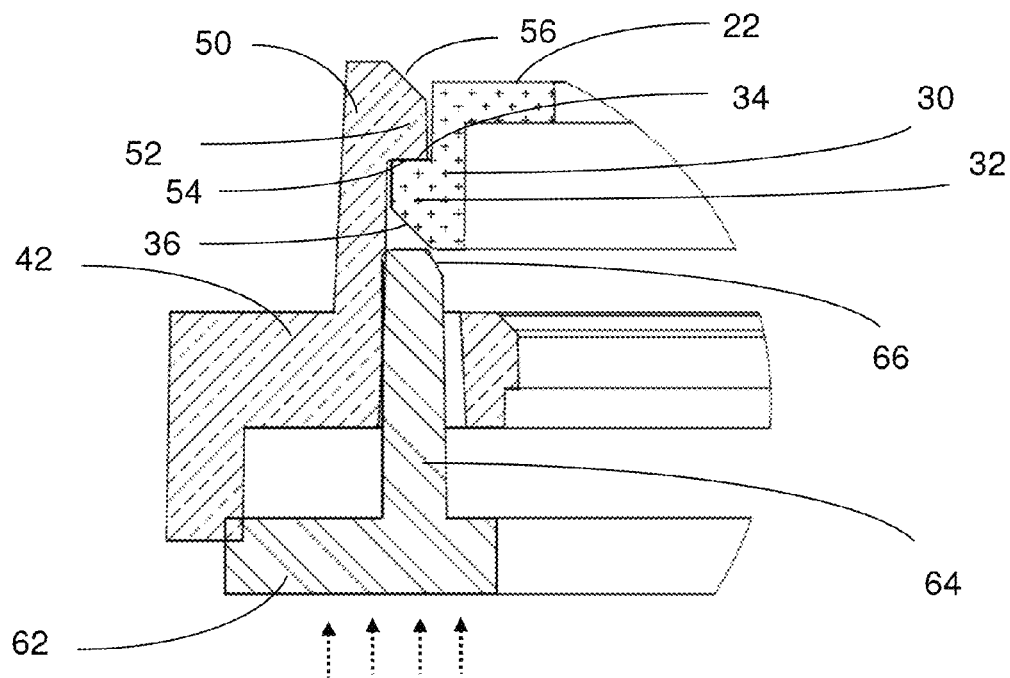
FIG. 15 depicts a close-up view of the cross-section of the vessel holder assembly of FIG. 14.
Figure 16:
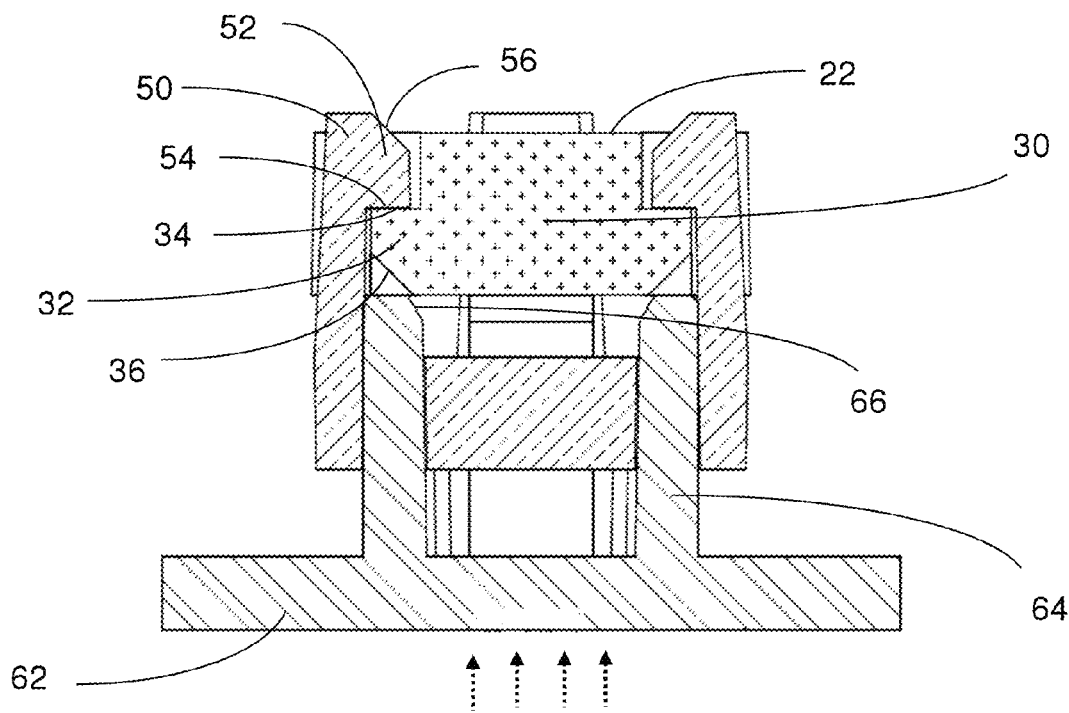
FIG. 16 shows another cross-sectional view of the vessel holder assembly of FIG. 13.

FIGS. 15-16 illustrate various cross-sectional views of the vessel holder assembly, where the cap assembly is attached to the vessel holder. In addition, the detachment tool 60 is placed in a position just prior to disengagement of the cap assembly from the vessel holder. As shown, the upright detachment members 64 are inserted within respective openings 46 of the vessel holder.

The upper surface 66 of each detachment member 64 is appropriately shaped so as to suitably engage with a corresponding attachment member 32 of the cap assembly. For instance, the upper surface 66 of each detachment member 64 includes a slanted portion that causes attachment members 32, 50 of the cap assembly and vessel holder to be pushed aside as the detachment member pushes up into the lower surface 34 of the protrusion 32.

As the detachment member 64 enters further through the opening 46, and into the vessel holder along the direction indicated by the dotted arrows, the attachment members 32, 50 are forced to move apart from one another. For instance, the upright attachment member 50 is pushed outwardly away from the corresponding sidewall 30 of the cap. Once clearance between the lower surface 54 of the attachment member 50 and the upper surface 34 of the protrusion 32 is established, the cap assembly may be easily removed from the vessel holder.

Though, it can be appreciated that other mechanisms through which the cap assembly and vessel holder may be locked may be employed. For example, the cap assembly and/or vessel holder may incorporate additional locking features, such as a complementary slot configuration, bayonet/pin assembly, keying elements and/or other arrangement(s) between components.

Figure 17:
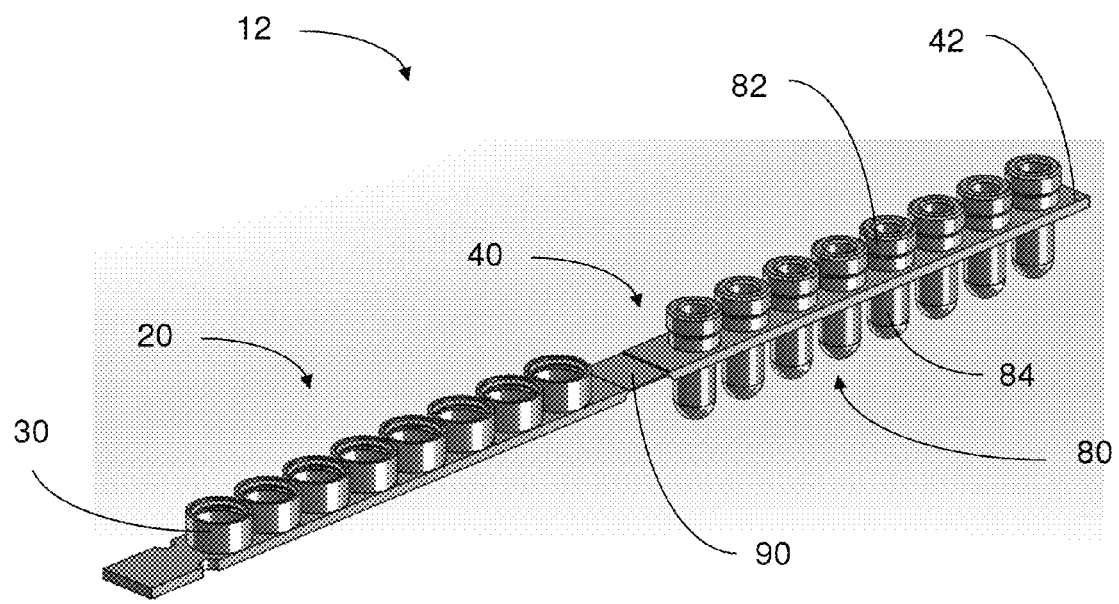
FIG. 17 depicts a perspective view of another vessel holder assembly in accordance with some embodiments.
Figure 18:
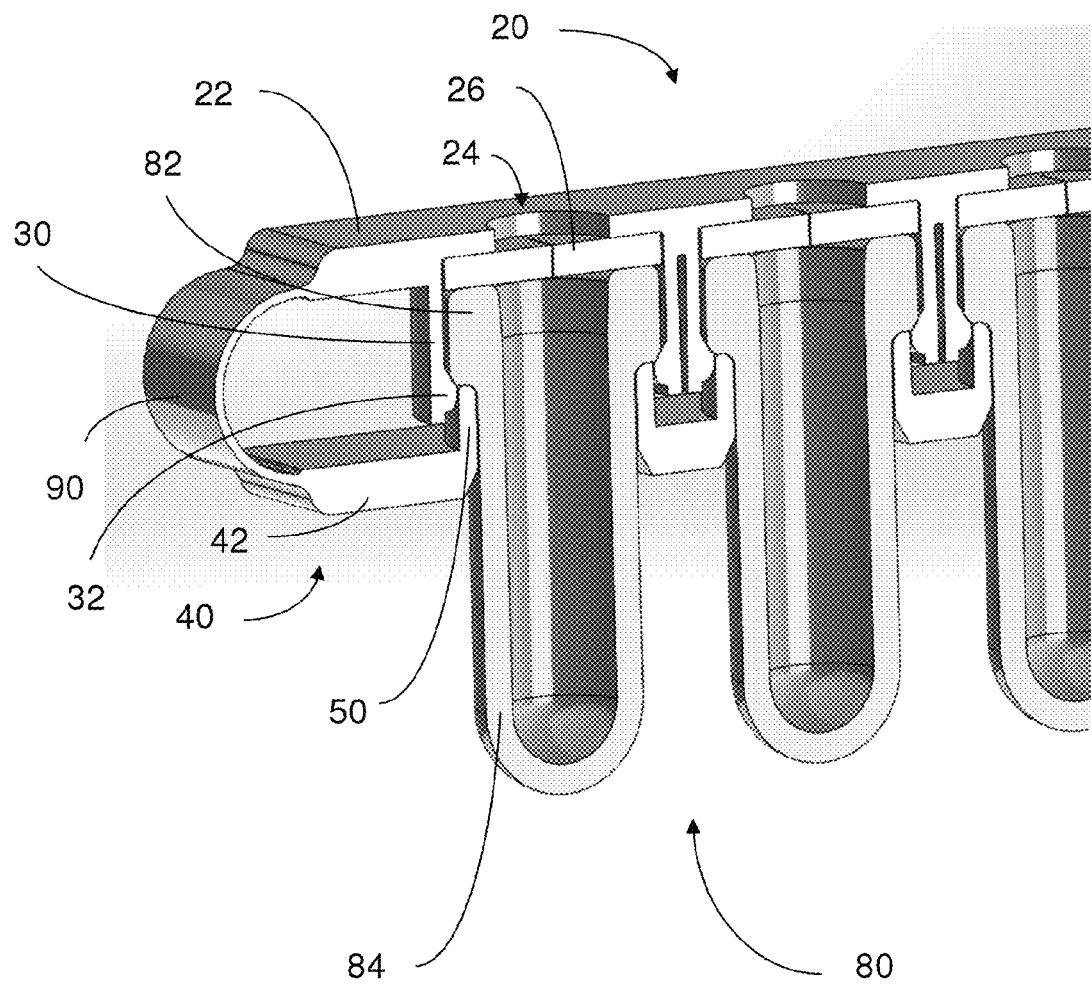
FIG. 18 illustrates a cross-section of a perspective view of yet another vessel holder assembly in accordance with some embodiments.
Figure 19:
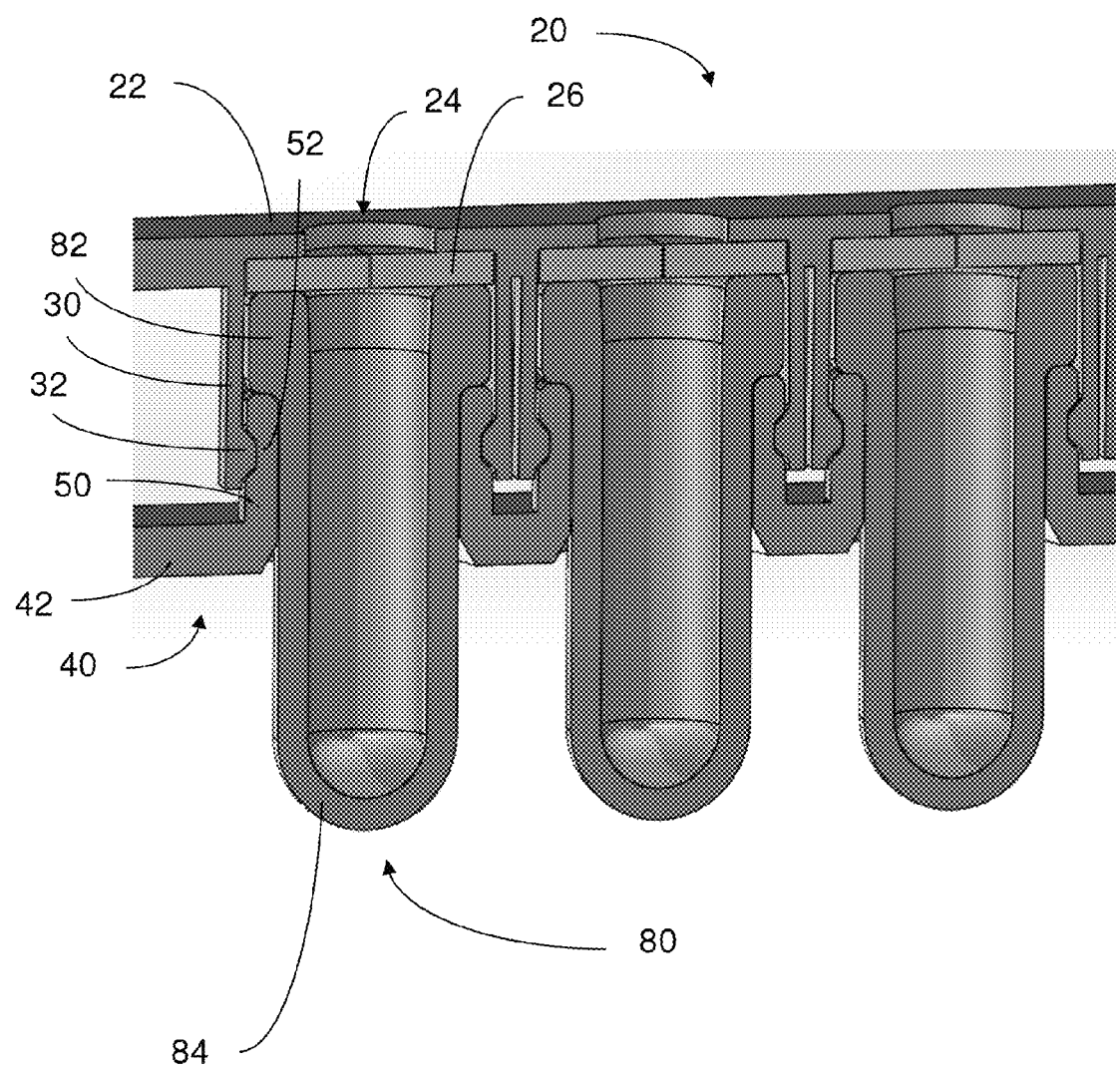
FIG. 19 depicts a cross-section of a perspective view of another vessel holder assembly in accordance with some embodiments.

FIGS. 17-19 illustrate further non-limiting embodiments of a vessel holder assembly 12. As shown in FIGS. 17-18, the cap assembly 20 and the vessel holder 40 are attached by a hinge 90, which allows for relative movement between the cap assembly and the vessel holder about the hinge.

FIGS. 18-19 show cross-sectional views of various embodiments in accordance with the present disclosure where the cap assembly 20 is attached to the vessel holder 40, and vessels 80 are disposed within receptacles of the vessel holder 40, or alternatively formed integrally therewith. In both embodiments, the upper flange 82 of each vessel 80 rests on an upright attachment member 50 of the vessel holder, with the cap assembly covering the entrance of each vessel. Each cap of the cap assembly is pressed on to the top surface of the vessel, with a rubber septum 26 disposed therebetween, so as to form a suitable seal.

In FIG. 18, the attachment members 32 of the cap assembly 20 extend as protrusions from the cap sidewalls 30. Though, in this embodiment, the attachment members 32 extend inwardly toward the vessel, so as to engage with both the attachment member 50 of the vessel holder as well as the upper flange 82 of the vessel. The attachment member 32 extends below and around the underside of the upper flange 82 so as to provide a snap fit arrangement. The attachment member 50 of the vessel holder 40 extends upright, so as to permit the underside of the upper flange 82 to rest thereon and also to be in contact, or otherwise engage, with the attachment member 32 of the cap assembly.

In some cases, upright attachment member 50 may provide a point of contact for downwardly extending attachment member 32, so as to allow for an appropriate seal attachment to form between the cap assembly and the vessel holder. In some embodiments, contact between respective attachment members 32, 50 results in a suitable attachment, for example, via adhesion or cohesion between the attachment members.

As discussed further above, and depicted in FIG. 19, attachment members 32, 50 may engage in a more structural arrangement. For instance, as shown, the attachment members 32 of the cap assembly 20 extend as protrusions from the cap sidewalls 30, and the attachment member 50 of the vessel holder 40 includes a recess 52 for receiving the protrusion 32. Also, the attachment member 50 of the vessel holder 40 extends upright, permitting the underside of the upper flange 82 to rest thereon. Though, while the attachment member 32 extends inwardly toward the vessel, the attachment member 32 does not contact the upper flange 82, or any other part of the vessel 80.

Figure 20:
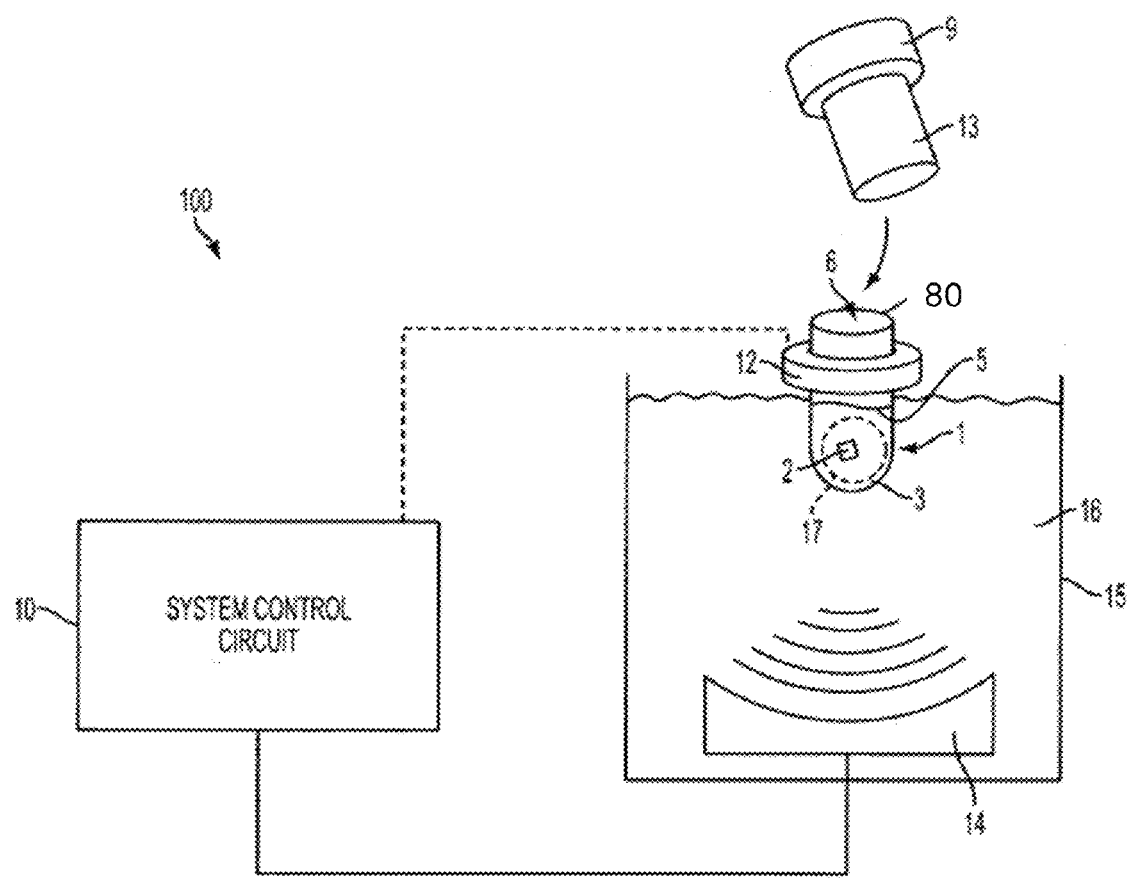
FIG. 20 shows a schematic block diagram of an acoustic treatment apparatus.

FIG. 20 shows a schematic block diagram of an acoustic treatment system 100 that incorporates or is used with one or more aspects of the present disclosure. Although embodiments described herein may include most or all aspects of the present disclosure, aspects of the invention may be used alone or in any suitable combination with other aspects of the invention. In some embodiments, vessel holder assemblies described herein may be used in conjunction with appropriate acoustic treatment systems.

In this illustrative embodiment, the acoustic treatment system 100 includes an acoustic transducer 14 (e.g., including one or more piezoelectric elements) that is capable of generating an acoustic field (e.g., at a focal zone 17) suitable to cause mixing, e.g., caused by cavitation, and/or other effects in a sample 1 contained in a vessel 80. The acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1, e.g., the focal zone 17 may fit entirely within the vessel 80. U.S. Pat. Nos. 6,948,843 and 6,719,449 are incorporated by reference herein for details regarding the construction and operation of an acoustic transducer and its control.

As discussed above, the focused acoustic energy may be used to treat sample material to yield desired results. For instance, for samples (e.g., tissue, blood, chemical formulations) that require processing for extraction, purification, or re-organization of components therein, focused acoustic energy may be used for a number of functions, such as lysing cells, fragmenting molecules (e.g., nucleic acids), creating emulsions/formulations, sterilizing material, separating components, or to provide any other suitable result. In some cases, focused acoustic energy may be used to suitably disassociate biological material from paraffin embedding, rehydrate tissue samples, mix enzymes, digest tissue samples, etc. Accordingly, by controlling the parameters of focused acoustic treatment, sample material may be processed in a variety of ways without having to transfer the sample between vessels, but rather, using a single vessel.

As also discussed above, the vessel 80 may have any suitable size or other arrangement, e.g., may be a glass tube, a plastic container, a well in a microtiter plate, a vial, or other, and may be supported at a location by a vessel holder 12, such as vessel holder assemblies in accordance with the present disclosure. In this embodiment, the vessel 80 is a 6×16 mm glass or plastic tube (approximately 150 microliter volume), but it should be understood that the vessel 80 may have any suitable shape, size, material, or other feature. For example, the vessel 80 may be a substantially cylindrical tube with a flat or curved bottom and a threaded top end to receive a cap 9, may include a cylindrical collar with a depending flexible bag-like portion to hold a sample, may be a single well in a multiwell plate, may be a cube-shaped vessel, or may be of any other suitable arrangement. The vessel 80 may be formed of glass, plastic, metal, composites, and/or any suitable combinations of materials, and formed by any suitable process, such as molding, machining, stamping, and/or a combination of processes.

The acoustic treatment system 100 may also include a coupling medium container 15 that is capable of holding a medium 16 (such as water or other liquid, gas, gel, solid, semi-solid, and/or a combination of such components) which transmits acoustic energy from the transducer 14 to the vessel 80. In some embodiments, the medium may also be provided as a cooling fluid for maintaining/controlling the temperature of sample material within the vessels. As discussed above, the vessel holder assembly may provide a sealed closure for the vessels while also allowing for substantial exposure of the vessels to the surrounding cooling fluid. For example, the cap assembly may remain an appropriate distance above the base of the vessel holder, while still providing the vessels with a seal, yet also permitting access of the cooling fluid to the vessels. In some cases, exposing the vessels to focused acoustic energy may make the vessels, and sample material located therein, prone to an increase in temperature. Thus, it would be beneficial to provide as much temperature-controlled fluid as possible surrounding each of the vessels.

In embodiments where the medium 16 includes a solid or semi-solid, a container 15 need not be provided or a portion of the medium 16 itself may function as a container 15, e.g., to hold a liquid or gas portion of the medium 16. For example, in one embodiment, the transducer 14 may be attached to a solid coupling medium 16 (such as a silica material), which is also attached to a vessel holder 12, which may be formed, at least in part, by an opening or other feature of the medium 16. Thus, the transducer 14, medium 16 and holder 12 may be formed as a single integrated part, if desired.

In some embodiments, the acoustic field may be controlled, the acoustic transducer 14 may be moved, and/or the vessel 80 may be moved (e.g., by way of moving a holder 12, such as a rack, tray, platform, etc., that supports the vessel 4) so that the sample is positioned in a desired location relative to the focal zone 17. In addition, or alternately, the transducer 14 may form the focal zone 17 so that the focal zone 17 is suitably positioned relative to the sample 1 or vessel 80.

To control the acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. As discussed in more detail below, the system control circuit 10 may control various other acoustic treatment system 100 functions, such as positioning of the vessel 80 and/or acoustic transducer 14 (a dashed line linking the control circuit 10 to the holder 12 schematically represents an optional positioning system, e.g., including a robot, gantry, screw drive, or other arrangement to move the holder 12), receiving operator input (such as commands for system operation), outputting information (e.g., to a visible display screen, indicator lights, sample treatment status information in electronic data form, and so on), and others.

In some embodiments, the vessel holder assembly 12 may serve to interface with the acoustic processing device so that the vessel 80 and the sample in the vessel is positioned in a known location relative to an acoustic field, for example, at least partially within a focal zone 17 of acoustic energy. Further, it should be appreciated that the vessel holder assembly 12 is not limited to devices like that shown and described herein, and may further, or instead, include a rack, slot, tray, gripper element, clamp, box or any other suitable arrangement, such as those described herein, for holding and/or moving the vessel 80 with respect to the focal zone 17.

As discussed above, in addition to being subject to focused acoustic energy, sample material located within the internal volume of the vessel(s) may be exposed to a suitable type and degree of electromagnetic irradiation (e.g., non-visible electromagnetic radiation, such as ultraviolet radiation, infrared radiation and/or microwave radiation). In some embodiments, such irradiation includes ultraviolet radiation, which has a wavelength shorter than that of visible light, but longer than X-rays; e.g., having a wavelength range between 10 nm and 400 nm. In some embodiments, irradiation includes microwave radiation, which has a wavelength longer than that of visible and infrared light; e.g., having a wavelength range between 1 mm and 1 m. For example, microwave irradiation may be used, at times, in cooperation with thermal heating, to fragment nucleic acids to size ranges suitable for sequencing.

Ultraviolet irradiation may employ a radiation wavelength and intensity that is appropriate for sterilizing sample material (e.g., killing cells, viruses, organisms, etc.) located within the vessel(s). It can be appreciated that irradiation in accordance with aspects of the present disclosure may include any suitable electromagnetic radiation, such as X-rays, gamma rays, infrared radiation, visible light, non-visible, electromagnetic radiation, microwave radiation, etc.

In some applications, it may be preferred, or required, that clinical preparations of biopharmaceuticals or bioactive agents derived from plasma, cell lines, blood samples, or tissues of human or animal origin be sterilized or otherwise free from contamination, or risk of contamination. Accordingly, in some embodiments, the system includes one or more suitable electromagnetic radiation sources (e.g., low-pressure mercury-vapor lamp for emitting ultraviolet radiation) that is effective for sterilizing material upon a sufficient degree of exposure (not shown in the figures). For example, the type of ultraviolet radiation emitted may fall within the Ultraviolet C (UVC) subtype category. In general, UVC radiation has a wavelength range of between 100-280 nm (energy per photon 4.43-12.4 eV) and energy output of between 5-200 $J/m^2$, or other parameter(s) known in the art, and is typically employed to kill microorganisms, such as bacteria, viruses, fungi, and others.

In some cases, the germicidal or virucidal nature of ultraviolet irradiation may be quite effective at wavelengths of between approximately 185 nm and 265 nm (e.g., 185 nm, 254 nm, 265 nm), particularly for inactivating viruses. Ultraviolet radiation within this wavelength range may be effective to degrade nucleic acids and, with a sufficient amount of exposure, is able to render a wide variety of viruses inactive. In some instances, while not necessarily the case in every situation, viruses that contain single-stranded nucleic acids may be more sensitive to ultraviolet radiation than viruses with double-stranded nucleic acids. This is due to the lack of a complementary strand in single-stranded nucleic acids, which results in an inability to repair damaged DNA/RNA. In some cases, as genome size increases, thereby increasing the overall likelihood of exposure to external effects/treatment (e.g., radiation, or other types of treatment), the sensitivity of a virus to ultraviolet radiation may also increase accordingly.

A sample, processed within the internal space of the vessel, may include any material. Exemplary samples include, but are not limited to, bones, teeth, blood, seeds, plants, pathological or non-pathological animal tissue (e.g., muscle, liver, kidney, lung, brain, pancreas, prostate, ovary, breast, etc.), tumor tissue, rocks, mineral samples, tree bark, and/or food products. Exemplary constituents include, but are not limited to, nucleic acids, amino acids, polypeptides, bacteria, viruses, fungi, spores, small organic molecules, small inorganic molecules, metals, minerals, ores, and the like. The sample may be relatively soft, such as a tissue sample, may be relatively hard, such as a bone or mineral sample, and may include sharp knife-like edges and/or sharp needle-like points. By way of a more particular example, a sample holder may be used to process pathological and/or non-pathological tissue or blood samples harvested from a patient. Such samples include, but are not limited to, putative tumor samples taking during a biopsy.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. It will be apparent that other embodiments and various modifications may be made to the present invention without departing from the scope thereof. The foregoing description of the invention is intended merely to be illustrative and not restrictive thereof. The scope of the present invention is defined by the appended claims and equivalents thereto.

The invention claimed is:

1. A vessel holder assembly, comprising:
a vessel holder including a base for holding a plurality of vessels, the vessel holder including at least one first attachment member located on the base; and
a cap assembly including a plurality of caps attached together, each cap arranged to cover an opening of a respective vessel held by the base, the cap assembly including at least one second attachment member complementary to a corresponding first attachment member such that engagement between the complementary first and second attachment members forms an attachment that resists relative movement between the cap assembly and the vessel holder away from one another,
wherein at least two pairs of corresponding first and second attachment members are located adjacent to each cap.

2. The vessel holder assembly of claim 1, wherein engagement between the complementary first and second attachment members forms a locked arrangement between the cap assembly and the vessel holder.

3. The vessel holder assembly of claim 1, wherein at least three pairs of corresponding first and second attachment members are located adjacent to each cap.

4. The vessel holder assembly of claim 1, wherein the vessel holder comprises a strip and first attachment members of the vessel holder are located along opposite sides of the strip.

5. The vessel holder assembly of claim 1, wherein each cap comprises an upper surface and a sidewall extending downwardly from the upper surface, the upper surface of the cap comprising an opening, and further comprising a septum located within a space defined by the upper surface and the sidewall of the cap.

6. The vessel holder assembly of claim 5, wherein the septum is attached to the cap and arranged to seal the opening of a respective vessel when the cap covers the opening of the vessel.

7. The vessel holder assembly of claim 5, wherein the at least one second attachment member comprises a protrusion extending outwardly from the sidewall of each cap for engaging a corresponding first attachment member of the vessel holder.

8. The vessel holder assembly of claim 1, wherein the at least one first attachment member comprises a protrusion extending inwardly from an outer surface of the base for engaging a corresponding attachment member of the cap assembly.

9. The vessel holder assembly of claim 1, wherein the attachment between complementary first and second attachment members is manually removable.

10. The vessel holder assembly of claim 1, wherein each of the second attachment members of the cap assembly comprises an arm extending downwardly from an upper surface of a cap, for engaging with a corresponding first attachment member of the vessel holder.

11. The vessel holder assembly of claim 1, further comprising an acoustic energy source spaced from and exterior to the plurality of vessels, configured to generate acoustic energy comprising a frequency of between about 100 kilohertz and about 100 megahertz and a focal zone having a width of less than about 2 centimeters.

12. The vessel holder assembly of claim 1, wherein each of the first attachment members extends upright relative to the base.

13. The vessel holder assembly of claim 12, wherein each of the first attachment members comprises a protrusion extending inwardly from an outer surface of the base, for engaging a corresponding second attachment member of the cap assembly.

14. The vessel holder assembly of claim 1, further comprising a plurality of septa, each septum attached to a respective one of the plurality of caps and arranged to seal the opening of a respective vessel when the cap covers the opening of the vessel.

15. The vessel holder assembly of claim 1, wherein each second attachment member comprises a protrusion extending outwardly from a sidewall of a corresponding one of the plurality of caps, for engaging a corresponding first attachment member of the vessel holder.

16. A vessel holder assembly, comprising:
a vessel holder including a base for holding a plurality of vessels, the vessel holder including at least one first attachment member located on the base; and
a cap assembly including a plurality of caps attached together, each cap arranged to cover an opening of a respective vessel held by the base, the cap assembly including at least one second attachment member complementary to a corresponding first attachment member such that engagement between the complementary first and second attachment members forms an attachment that resists relative movement between the cap assembly and the vessel holder away from one another,
wherein the cap assembly comprises a strip and second attachment members of the cap assembly are located between adjacent caps.

17. The vessel holder assembly of claim 16, wherein engagement between the complementary first and second attachment members forms a locked arrangement between the cap assembly and the vessel holder.

18. The vessel holder assembly of claim 16, wherein at least two pairs of corresponding first and second attachment members are located adjacent to each cap.

19. The vessel holder assembly of claim 16, wherein the first attachment members of the vessel holder are located along opposite sides of the strip.

20. The vessel holder assembly of claim 16, wherein each of the plurality of caps comprises an upper surface and a sidewall extending downwardly from the upper surface, the upper surface of each cap comprising an opening, and further comprising a septum located within a space defined by the upper surface and the sidewall of each of the plurality of caps.

21. The vessel holder assembly of claim 20, wherein the septum of each cap is arranged to seal the opening of a respective vessel when the cap covers the opening of the vessel.

22. The vessel holder assembly of claim 16, wherein the at least one second attachment member comprises a protrusion extending outwardly from a sidewall of each of the plurality of caps for engaging a corresponding first attachment member of the vessel holder.

23. The vessel holder assembly of claim 16, wherein the at least one first attachment member comprises a protrusion extending inwardly from an outer surface of the base for engaging a corresponding second attachment member of the cap assembly.

24. The vessel holder assembly of claim 16, wherein the attachment between complementary first and second attachment members is manually removable.

25. The vessel holder assembly of claim 16, wherein each of the second attachment members of the cap assembly comprises an arm extending downwardly from an upper surface of a cap, for engaging with a corresponding first attachment member of the vessel holder.

26. The vessel holder assembly of claim 16, further comprising an acoustic energy source spaced from and exterior to the plurality of vessels, configured to generate acoustic energy comprising a frequency of between about 100 kilohertz and about 100 megahertz and a focal zone having a width of less than about 2 centimeters.

27. The vessel holder assembly of claim 16, wherein each of the first attachment members extends upright relative to the base.

28. The vessel holder assembly of claim 27, wherein each of the first attachment members comprises a protrusion extending inwardly from an outer surface of the base, for engaging a corresponding second attachment member of the cap assembly.

29. The vessel holder assembly of claim 16, further comprising a plurality of septa, each septum attached to a respective one of the plurality of caps and arranged to seal the opening of a respective vessel when the cap covers the opening of the vessel.

30. The vessel holder assembly of claim 16, wherein each second attachment member comprises a protrusion extending outwardly from a sidewall of a corresponding one of the plurality of caps, for engaging a corresponding first attachment member of the vessel holder, wherein each of the first attachment members extends upright relative to the base.

31. A vessel holder assembly, comprising:
a vessel holder including a base for holding a plurality of vessels, the vessel holder including at least one first attachment member located on the base, the vessel holder including at least one detachment opening for receiving a corresponding detachment member, each detachment opening located adjacent to a respective first attachment member;
a cap assembly including a plurality of caps attached together, each cap arranged to cover an opening of a respective vessel held by the base, the cap assembly including at least one second attachment member complementary to a corresponding first attachment member such that engagement between the complementary first and second attachment members forms an attachment that resists relative movement between the cap assembly and the vessel holder away from one another; and
a detachment tool including:
a base having a plurality of openings, and
at least one detachment member, each detachment member extending upright relative to the base and positioned for alignment with respect to a corresponding detachment opening, for disengaging respective first and second attachment members of the cap and the vessel holder.

* * * * *